(12) United States Patent
Scheiner et al.

(10) Patent No.: US 11,266,837 B2
(45) Date of Patent: Mar. 8, 2022

(54) POSITION SENSITIVE LINGUAL MUSCLE SIMULATION SYSTEM FOR OBSTRUCTIVE SLEEP APNEA

(71) Applicant: Medtronic Xomed, LLC, Jacksonville, FL (US)

(72) Inventors: Avram Scheiner, Vadnais Heights, MN (US); James Hissong, Jacksonville, FL (US)

(73) Assignee: MEDTRONIC XOMED, INC., Jacksonville, FL (US)

( * ) Notice: Subject to any disclaimer, the term of this patent is extended or adjusted under 35 U.S.C. 154(b) by 0 days.

(21) Appl. No.: 16/752,371

(22) Filed: Jan. 24, 2020

(65) Prior Publication Data
US 2020/0282219 A1 Sep. 10, 2020

Related U.S. Application Data

(60) Provisional application No. 62/814,398, filed on Mar. 6, 2019.

(51) Int. Cl.
*A61N 1/36* (2006.01)
*A61N 1/02* (2006.01)
(Continued)

(52) U.S. Cl.
CPC .......... *A61N 1/3611* (2013.01); *A61B 5/0004* (2013.01); *A61B 5/0015* (2013.01);
(Continued)

(58) Field of Classification Search
CPC .. A61N 1/3611; A61N 1/025; A61N 1/36003; A61N 1/3601; A61N 1/36078;
(Continued)

(56) References Cited

U.S. PATENT DOCUMENTS

| 2,999,232 A | 9/1961 | Wilson |
| 3,032,029 A | 5/1962 | Cunningham |

(Continued)

FOREIGN PATENT DOCUMENTS

| EP | 3355984 A1 | 8/2018 |
| WO | 9215364 A1 | 9/1992 |

(Continued)

OTHER PUBLICATIONS

PCT Search Report and Written opinion issued in PCT Application No. PCT/US2020/021245 dated Jun. 16, 2020, 15 pages.

(Continued)

*Primary Examiner* — Erin M Piateski
(74) *Attorney, Agent, or Firm* — Shumaker & Sieffert, P.A.

(57) ABSTRACT

An implantable neurostimulator (INS) and method of use, the INS including an electrical lead having formed thereon at least a pair of bi-polar electrodes, wherein the electrical lead is configured for placement of the pair of bi-polar electrodes proximate protrusor muscles of a patient, a pulse generator electrically connected to the electrical lead and configured to deliver electrical energy to the pair of bi-polar electrodes, the pulse generator having mounted therein a sensor and a control circuit, and the sensor is configured to generate signals representative of an orientation of the pulse generator and communicate the signals to the control circuit and the control circuit is configured to determine the orientation of the pulse generator and deliver electrical energy to the bi-polar electrodes when the determined orientation correlates to a pre-determined orientation.

18 Claims, 6 Drawing Sheets

(51) Int. Cl.
*A61N 1/372* (2006.01)
*A61F 5/56* (2006.01)
*A61B 5/00* (2006.01)
A61B 5/024 (2006.01)
A61B 5/11 (2006.01)
A61B 7/02 (2006.01)
A61B 5/389 (2021.01)

(52) U.S. Cl.
CPC .......... *A61B 5/0031* (2013.01); *A61B 5/4818* (2013.01); *A61B 5/7264* (2013.01); *A61F 5/566* (2013.01); *A61N 1/025* (2013.01); *A61N 1/3601* (2013.01); *A61N 1/36003* (2013.01); *A61N 1/36078* (2013.01); *A61N 1/36125* (2013.01); *A61N 1/36139* (2013.01); *A61N 1/37247* (2013.01); *A61N 1/37252* (2013.01); *A61B 5/024* (2013.01); *A61B 5/1116* (2013.01); *A61B 5/389* (2021.01); *A61B 7/023* (2013.01); *A61B 2562/0219* (2013.01); *A61N 1/36175* (2013.01)

(58) Field of Classification Search
CPC ............ A61N 1/36125; A61N 1/36139; A61N 1/37247; A61N 1/37252; A61N 1/36175; A61B 5/0004; A61B 5/0015; A61B 5/0031; A61B 5/4818; A61B 5/7264; A61B 5/389; A61B 5/024; A61B 5/1116; A61B 7/023; A61B 2562/0219; A61F 5/566
USPC ......................................................... 607/42
See application file for complete search history.

(56) References Cited

U.S. PATENT DOCUMENTS

| | | |
|---|---|---|
| 3,480,010 A | 11/1969 | Crossley |
| 3,593,703 A | 7/1971 | Gunn et al. |
| 3,696,377 A | 10/1972 | Wall |
| 3,998,209 A | 12/1976 | Macvaugh |
| 4,220,142 A | 9/1980 | Rosen et al. |
| 4,304,227 A | 12/1981 | Samelson |
| 4,551,473 A | 11/1985 | Schossow |
| 4,593,686 A | 6/1986 | Lloyd et al. |
| 4,655,213 A | 4/1987 | Rapoport et al. |
| 4,830,008 A | 5/1989 | Meer |
| 4,989,617 A | 2/1991 | Memberg et al. |
| 5,065,756 A | 11/1991 | Rapoport |
| 5,123,425 A | 6/1992 | Shannon, Jr. et al. |
| 5,146,918 A | 9/1992 | Kallok et al. |
| 5,335,654 A | 8/1994 | Rapoport |
| 5,365,945 A | 11/1994 | Halstrom |
| 5,522,862 A | 6/1996 | Testerman et al. |
| 5,540,733 A | 7/1996 | Testerman et al. |
| 6,041,784 A | 3/2000 | Halstrom |
| 6,044,297 A | 3/2000 | Sheldon et al. |
| 6,161,542 A | 12/2000 | Halstrom |
| 6,212,435 B1 | 4/2001 | Lattner et al. |
| 6,251,126 B1 | 6/2001 | Ottenhoff et al. |
| 6,269,269 B1 | 7/2001 | Ottenhoff et al. |
| 6,536,439 B1 | 3/2003 | Palmisano |
| 6,587,725 B1 | 7/2003 | Durand et al. |
| 6,618,627 B2 | 9/2003 | Lattner et al. |
| 6,635,021 B1 | 10/2003 | Sullivan et al. |
| 6,666,830 B1 | 12/2003 | Lehrman et al. |
| 6,770,037 B2 | 8/2004 | Sullivan et al. |
| 6,818,665 B2 | 11/2004 | Wennerholm et al. |
| 6,935,335 B1 | 8/2005 | Lehrman et al. |
| 7,004,908 B2 | 2/2006 | Sullivan et al. |
| 7,212,862 B2 | 5/2007 | Park et al. |
| 7,225,021 B1 | 5/2007 | Park et al. |
| 7,311,103 B2 | 12/2007 | Jeppesen |
| 7,322,356 B2 | 1/2008 | Critzer et al. |
| 7,469,698 B1 | 12/2008 | Childers et al. |
| 7,473,227 B2 | 1/2009 | Hsu et al. |
| 7,509,164 B2 | 3/2009 | Jensen et al. |
| 7,520,277 B1 | 4/2009 | Grady |
| 7,540,843 B2 | 6/2009 | Backer |
| 7,678,058 B2 | 3/2010 | Patangay et al. |
| 7,711,438 B2 | 5/2010 | Lattner et al. |
| 7,725,195 B2 | 5/2010 | Lima et al. |
| 7,789,837 B2 | 9/2010 | Lehrman et al. |
| 7,819,823 B2 | 10/2010 | Lehrman et al. |
| 7,926,486 B2 | 4/2011 | Childers |
| 7,937,159 B2 | 5/2011 | Lima et al. |
| 8,187,200 B2 | 5/2012 | Jensen et al. |
| 8,220,457 B2 | 7/2012 | Berthon-Jones et al. |
| 8,220,467 B2 | 7/2012 | Sanders |
| 8,307,831 B2 | 11/2012 | Rousseau |
| 8,333,696 B2 | 12/2012 | Levendowski et al. |
| 8,359,097 B2 | 1/2013 | Alt et al. |
| 8,359,108 B2 | 1/2013 | McCreery |
| 8,413,661 B2 | 4/2013 | Rousseau et al. |
| 8,428,727 B2 | 4/2013 | Bolea et al. |
| 8,486,947 B2 | 7/2013 | Schwartz et al. |
| 8,545,231 B2 | 10/2013 | Lloyd et al. |
| 8,545,416 B1 | 10/2013 | Kayyali et al. |
| 8,561,616 B2 | 10/2013 | Rousseau et al. |
| 8,569,374 B2 | 10/2013 | Veasey |
| 8,574,164 B2 | 11/2013 | Mashiach |
| 8,577,464 B2 | 11/2013 | Mashiach |
| 8,577,465 B2 | 11/2013 | Mashiach |
| 8,577,466 B2 | 11/2013 | Mashiach |
| 8,577,467 B2 | 11/2013 | Mashiach et al. |
| 8,577,468 B2 | 11/2013 | Mashiach et al. |
| 8,577,472 B2 | 11/2013 | Mashiach et al. |
| 8,577,478 B2 | 11/2013 | Mashiach et al. |
| 8,585,617 B2 | 11/2013 | Mashiach et al. |
| 8,588,941 B2 | 11/2013 | Mashiach |
| 8,644,939 B2 | 2/2014 | Wilson et al. |
| 8,644,947 B2 | 2/2014 | Zhu et al. |
| 8,700,183 B2 | 4/2014 | Mashiach |
| 8,718,776 B2 | 5/2014 | Mashiach et al. |
| 8,740,805 B2 | 6/2014 | Lehrman et al. |
| 8,751,005 B2 | 6/2014 | Meadows et al. |
| 8,753,327 B2 | 6/2014 | Fan |
| 8,781,587 B2 | 7/2014 | Alt et al. |
| 8,783,258 B2 | 7/2014 | Jacobs et al. |
| 8,808,158 B2 | 8/2014 | Harrison et al. |
| 8,812,113 B2 | 8/2014 | Mashiach |
| 8,812,135 B2 | 8/2014 | Mashiach |
| 8,813,753 B2 | 8/2014 | Bhat et al. |
| 8,831,730 B2 | 9/2014 | Mashiach et al. |
| 8,838,256 B2 | 9/2014 | Mashiach et al. |
| 8,886,322 B2 | 11/2014 | Meadows et al. |
| 8,892,205 B2 | 11/2014 | Miller, III et al. |
| 8,897,880 B2 | 11/2014 | Mashiach |
| 8,903,515 B2 | 11/2014 | Mashiach |
| 8,909,341 B2 | 12/2014 | Gelfand et al. |
| 8,925,551 B2 | 1/2015 | Sanders |
| 8,948,871 B2 | 2/2015 | Mashiach et al. |
| 8,958,893 B2 | 2/2015 | Mashiach |
| 8,999,658 B2 | 4/2015 | Gozal et al. |
| 9,011,341 B2 | 4/2015 | Jensen et al. |
| 9,031,653 B2 | 5/2015 | Mashiach |
| 9,061,162 B2 | 6/2015 | Mashiach et al. |
| 9,072,613 B2 | 7/2015 | Shantha |
| 9,077,022 B2 | 7/2015 | Howard et al. |
| 9,078,634 B2 | 7/2015 | Gonzales et al. |
| 9,095,471 B2 | 8/2015 | Iyer et al. |
| 9,095,725 B2 | 8/2015 | Mashiach |
| 9,114,256 B2 | 8/2015 | Achhab et al. |
| 9,144,511 B2 | 9/2015 | Rousseau et al. |
| 9,155,899 B2 | 10/2015 | Mashiach et al. |
| 9,186,504 B2 | 11/2015 | Gross |
| 9,254,219 B2 | 2/2016 | Shantha |
| 9,295,670 B2 | 3/2016 | Fan |
| 9,326,886 B2 | 5/2016 | Rousseau |
| 9,402,563 B2 | 8/2016 | Thakur et al. |
| 9,403,009 B2 | 8/2016 | Mashiach |
| 9,409,013 B2 | 8/2016 | Mashiach et al. |
| 9,415,215 B2 | 8/2016 | Mashiach |

(56) References Cited

U.S. PATENT DOCUMENTS

| | | |
|---|---|---|
| 9,415,216 B2 | 8/2016 | Mashiach |
| 9,435,814 B2 | 9/2016 | Gozal et al. |
| 9,492,086 B2 | 11/2016 | Ewers et al. |
| 9,526,652 B2 | 12/2016 | Harrison et al. |
| 9,533,114 B1 | 1/2017 | Kayyali et al. |
| 9,545,331 B2 | 1/2017 | Ingemarsson-Matzen |
| 9,561,012 B2 | 2/2017 | Hirabayashi |
| 9,655,767 B1 | 5/2017 | Harrison et al. |
| 9,662,045 B2 | 5/2017 | Skelton et al. |
| 9,687,383 B2 | 6/2017 | Ngemarsson-Matzen |
| 9,744,354 B2 | 8/2017 | Bolea et al. |
| 9,855,164 B2 | 1/2018 | Weadock et al. |
| 9,883,847 B2 | 2/2018 | Wolf et al. |
| 9,889,299 B2 | 2/2018 | Ni et al. |
| 10,022,262 B2 | 7/2018 | Irwin et al. |
| 10,029,098 B2 | 7/2018 | Papay |
| 10,111,774 B2 | 10/2018 | Gonzales et al. |
| 10,123,900 B2 | 11/2018 | Mohan et al. |
| 10,149,621 B2 | 12/2018 | Yoon et al. |
| 10,166,268 B2 | 1/2019 | Mendelowitz et al. |
| 10,172,920 B2 | 1/2019 | Braley et al. |
| 10,195,428 B2 | 2/2019 | Scheiner |
| 10,206,571 B2 | 2/2019 | Ewers et al. |
| 10,231,650 B2 | 3/2019 | Skelton et al. |
| 10,314,736 B2 | 6/2019 | Catalano |
| 10,368,800 B2 | 8/2019 | Qiu |
| 10,406,306 B2 | 9/2019 | Whiting et al. |
| 10,500,086 B1 | 12/2019 | Harrison et al. |
| 10,543,119 B2 | 1/2020 | Ingemarsson-Matzen |
| 10,569,037 B2 | 2/2020 | O'Day |
| 10,575,981 B2 | 3/2020 | Rayek et al. |
| 10,617,694 B2 | 4/2020 | Hedner et al. |
| 10,632,009 B2 | 4/2020 | Goff et al. |
| 10,675,467 B2 | 6/2020 | Papay |
| 2002/0049479 A1 | 4/2002 | Pitts |
| 2003/0069626 A1 | 4/2003 | Lattner et al. |
| 2007/0150006 A1 | 6/2007 | Libbus et al. |
| 2008/0103407 A1 | 5/2008 | Bolea et al. |
| 2009/0078274 A1 | 3/2009 | Bhat et al. |
| 2010/0010385 A1 | 1/2010 | Skelton et al. |
| 2010/0087896 A1 | 4/2010 | McCreery |
| 2010/0174341 A1 | 7/2010 | Bolea et al. |
| 2010/0204614 A1 | 8/2010 | Lindquist et al. |
| 2011/0093036 A1 | 4/2011 | Mashiach |
| 2011/0152965 A1 | 6/2011 | Mashiach et al. |
| 2013/0030497 A1* | 1/2013 | Karamanoglu ........ A61B 5/686 607/42 |
| 2013/0042876 A1 | 2/2013 | Hermanson et al. |
| 2013/0072747 A1 | 3/2013 | Mashiach |
| 2013/0072999 A1 | 3/2013 | Mashiach |
| 2013/0079843 A1 | 3/2013 | Mashiach |
| 2013/0085537 A1 | 4/2013 | Mashiach |
| 2013/0085540 A1 | 4/2013 | Mashiach et al. |
| 2013/0085541 A1 | 4/2013 | Mashiach |
| 2013/0085542 A1 | 4/2013 | Mashiach |
| 2013/0085543 A1 | 4/2013 | Mashiach et al. |
| 2013/0085544 A1 | 4/2013 | Mashiach |
| 2013/0085545 A1 | 4/2013 | Mashiach |
| 2013/0085558 A1 | 4/2013 | Mashiach |
| 2013/0085559 A1 | 4/2013 | Mashiach |
| 2013/0085560 A1 | 4/2013 | Mashiach |
| 2013/0085561 A1 | 4/2013 | Mashiach |
| 2014/0031840 A1 | 1/2014 | Mashiach |
| 2014/0031889 A1 | 1/2014 | Mashiach |
| 2014/0031890 A1 | 1/2014 | Mashiach et al. |
| 2014/0031891 A1 | 1/2014 | Mashiach |
| 2014/0031892 A1 | 1/2014 | Mashiach |
| 2014/0031913 A1 | 1/2014 | Mashiach |
| 2014/0031914 A1 | 1/2014 | Mashiach |
| 2014/0031915 A1 | 1/2014 | Mashiach et al. |
| 2014/0031916 A1 | 1/2014 | Mashiach |
| 2014/0039579 A1 | 2/2014 | Mashiach et al. |
| 2014/0052212 A1 | 2/2014 | Mashiach et al. |
| 2014/0107727 A1 | 4/2014 | Mashiach |
| 2014/0135868 A1 | 5/2014 | Bashyam |
| 2014/0228905 A1* | 8/2014 | Bolea ...................... A61F 5/56 607/42 |
| 2014/0323839 A1 | 10/2014 | McCreery |
| 2014/0358189 A1 | 12/2014 | Mashiach et al. |
| 2014/0371822 A1 | 12/2014 | Mashiach et al. |
| 2014/0371823 A1 | 12/2014 | Mashiach et al. |
| 2014/0371824 A1 | 12/2014 | Mashiach et al. |
| 2015/0190630 A1 | 7/2015 | Kent et al. |
| 2015/0224307 A1 | 8/2015 | Bolea |
| 2016/0030739 A1 | 2/2016 | Mashiach |
| 2016/0030740 A1 | 2/2016 | Mashiach |
| 2016/0354603 A1* | 12/2016 | Keenan ................ A61N 1/3611 |
| 2017/0197075 A1 | 7/2017 | Bruggen et al. |
| 2017/0290699 A1 | 10/2017 | Radmand |
| 2017/0296815 A1 | 10/2017 | Papay |
| 2018/0221660 A1 | 8/2018 | Suri et al. |
| 2019/0117967 A1 | 4/2019 | Scheiner |
| 2020/0281763 A1 | 9/2020 | Scheiner |
| 2020/0282215 A1 | 9/2020 | Scheiner et al. |

FOREIGN PATENT DOCUMENTS

| | | |
|---|---|---|
| WO | 2010090852 A2 | 8/2010 |
| WO | 2011016864 A1 | 2/2011 |
| WO | 2017059072 A1 | 4/2017 |

OTHER PUBLICATIONS

Sanders et al., "Three-Dimensional Atlas of Human Tongue Muscles," The Anatomical Record 296:1102-1114 (2013), 14 pages.

International Preliminary Report on Patentability from International Application No. PCT/US202/021245, dated Sep. 16, 2021, 9 pp.

* cited by examiner

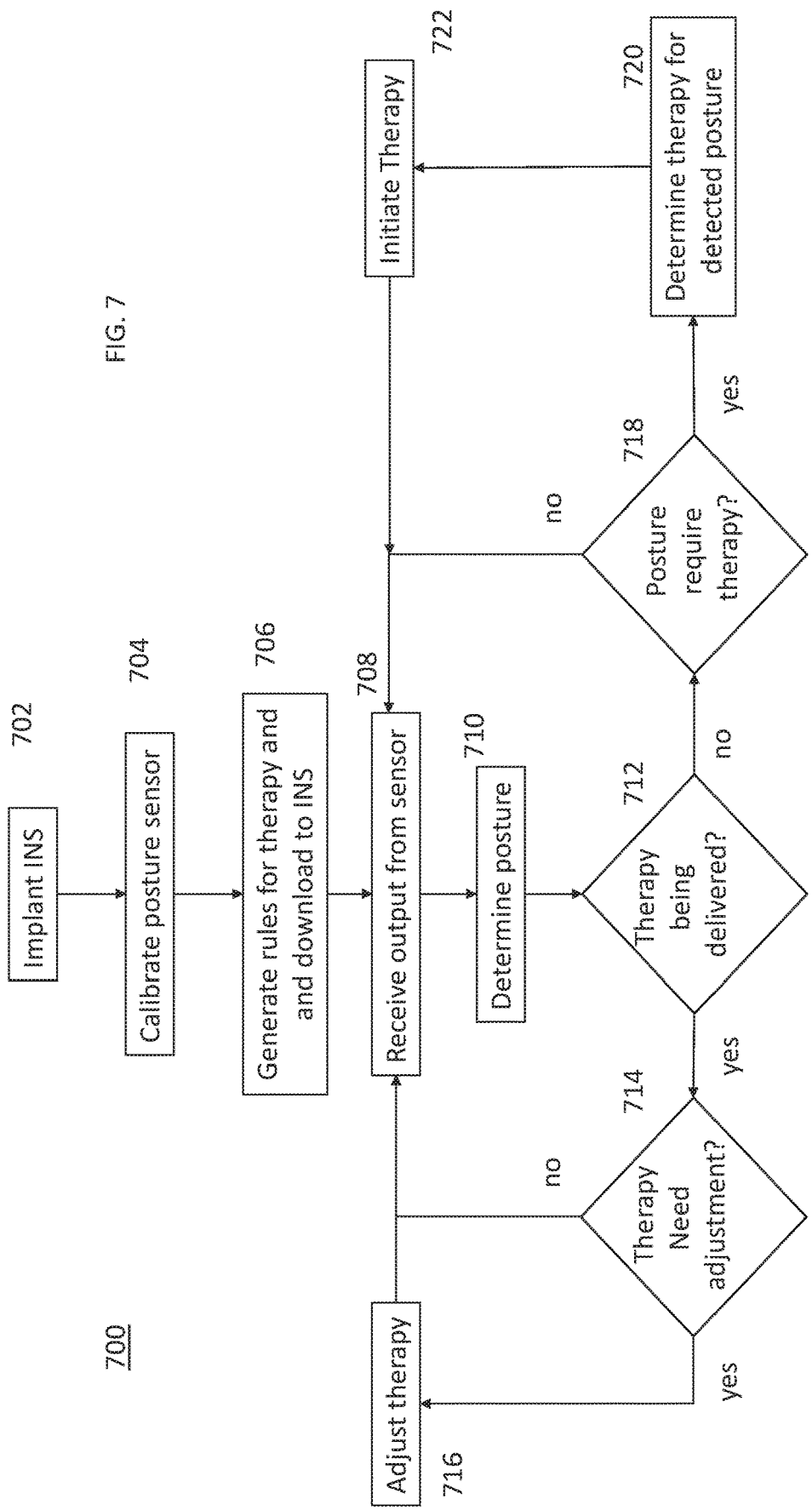

POSITION SENSITIVE LINGUAL MUSCLE SIMULATION SYSTEM FOR OBSTRUCTIVE SLEEP APNEA

CROSS-REFERENCE TO RELATED APPLICATION

This application claims priority to U.S. Provisional Application No. 62/814,398 filed Mar. 6, 2019 and entitled INTRAMUSCULAR HYPOGLOSSAL NERVE STIMULATION FOR OBSTRUCTIVE SLEEP APNEA THERAPY, the entire contents of which are incorporated herein by reference.

TECHNICAL FIELD

This disclosure relates to a medical device system and method for therapeutic electrical stimulation of the lingual muscles for treatment of obstructive sleep apnea. More particularly this disclosure is directed to systems and methods for determining a patient's position and utilization of this determination to initiate therapy.

BACKGROUND

Implantable medical devices capable of delivering electrical stimulation pulses have been proposed or are available for treating a variety of medical conditions, such as cardiac arrhythmias and chronic pain as examples. Obstructive sleep apnea (OSA), which encompasses apnea and hypopnea, is a serious disorder in which breathing is irregularly and repeatedly stopped and started during sleep, resulting in disrupted sleep and reducing blood oxygen levels. OSA is caused by complete or partial collapse of the pharynx during sleep. In particular, muscles in a patient's throat intermittently relax thereby obstructing the upper airway while sleeping. Airflow into the upper airway can be obstructed by the tongue or soft pallet moving to the back of the throat and covering a smaller than normal airway. Loss of air flow also causes unusual inter-thoracic pressure as a person tries to breathe with a blocked airway. Lack of adequate levels of oxygen during sleep can contribute to abnormal heart rhythms, heart attack, heart failure, high blood pressure, stroke, memory problems and increased accidents. Additionally, loss of sleep occurs when a person is awakened during an apneic episode. Implantable medical devices capable of delivering electrical stimulation pulses have been proposed for treating OSA by electrically stimulating muscles around the upper airway that may block the airway during sleep.

SUMMARY

One aspect of the disclosure is directed to an implantable neurostimulator (INS) including: an electrical lead having formed thereon at least a pair of bi-polar electrodes, where the electrical lead is configured for placement of the pair of bi-polar electrodes proximate protrusor muscles of a patient; a pulse generator electrically connected to the electrical lead and configured to deliver electrical energy to the pair of bi-polar electrodes, the pulse generator having mounted therein a sensor and a control circuit, where the sensor is configured to generate signals representative of an orientation of the pulse generator and communicate the signals to the control circuit and the control circuit is configured to determine the orientation of the pulse generator and deliver electrical energy to the bi-polar electrodes when the determined orientation correlates to a pre-determined orientation.

Other embodiments of this aspect include corresponding computer systems, apparatus, and computer programs recorded on one or more computer storage devices, each configured to perform the actions of the methods and systems described herein.

Implementations of this aspect of the disclosure may include one or more of the following features. The implantable neurostimulator where the sensor is a three-axis accelerometer. The implantable neurostimulator where the determined orientation is indicative a patient in which the INS is implanted is supine. The implantable neurostimulator further including a memory storing therein a correlation of the signals from the sensor to orientations of the pulse generator. The implantable neurostimulator where the memory stores therein a plurality of stimulation control parameters. The implantable neurostimulator where each stimulation control parameter is associated with an orientation of the pulse generator. The implantable neurostimulator where the sensor is further configured to detect one or more of motion, heartrate, or sound. The implantable neurostimulator where the control circuit delivers electrical energy to the bi-polar electrodes when the determined orientation correlates to a pre-determined orientation and one or more of a detected motion, heartrate, or sound correspond to a determination that the patient is asleep or in need of therapy. The implantable neurostimulator where the sensor and control circuit are configured to detect electromyography signals of the protrusor muscles. The implantable neurostimulator where the control circuit is configured to determine a fatigue of the protrusor muscles based on the detected electromyography signals.

A further aspect of the disclosure is directed to a method including: correlating the postures of a patient to an orientation of an implanted neurostimulator (INS), receiving sensor data indicative of the INS being in an orientation that correlates to a posture in which the patient is likely to experience obstructive sleep apnea, determining whether the patient is in a sleep state or in need of therapy, and delivering electrical energy to a pair of bi-polar electrodes to activate a patient's protrusor muscles. Other embodiments of this aspect include corresponding computer systems, apparatus, and computer programs recorded on one or more computer storage devices, each configured to perform the actions of the methods and systems described herein.

Implementations of this aspect of the disclosure may include one or more of the following features. The method where the sensor is a three-axis accelerometer. The method where the detected orientation of the INS is indicative of a posture in which the patient is supine. The method further including storing in memory in the INS a correlation of the received sensor data to postures of the patient. The method further including storing in memory a plurality of stimulation control parameters. The method where each stimulation control parameter is associated with an orientation of the INS. The method further including detecting one or more of motion, heartrate, or sound. The method further including determining the patient is in a sleep state or in need of therapy based on the sensor data indicative of the INS orientation and one or more of the detected motion, heartrate, or sound. The method further including detecting electromyography signals of the protrusor muscles. The method further including the control circuit determining fatigue of the protrusor muscles based on the detected electromyography signals. Implementations of the described techniques may include hardware, a method or process, or computer software on a computer-accessible medium, including software, firmware, hardware, or a combination of them Installed on the system that in operation causes or cause the system to perform the actions. One or more computer programs can be configured to perform particular operations or actions by virtue of including Instructions that, when executed by data processing apparatus, cause the apparatus to perform the actions.

BRIEF DESCRIPTION OF THE DRAWINGS

FIG. 7 is a flow chart describing a method of the disclosure.

DETAILED DESCRIPTION

Figure 1:
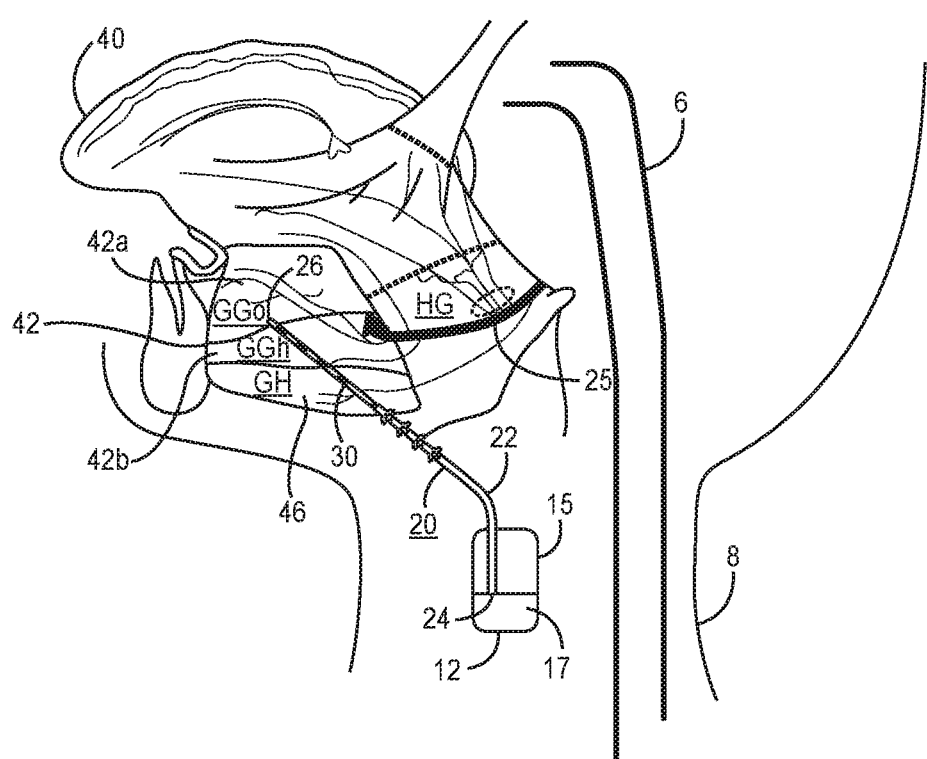
FIG. 1 is a conceptual diagram of an implantable neurostimulator (INS) for delivering OSA therapy.

A medical device system for delivering electrical stimulation to the lingual muscles of the tongue, specifically the protrusor muscles, for the treatment of OSA is described herein. Electrical stimulation is delivered to cause the tongue of a patient to be in a protruded state, during sleep, to avoid or reduce upper airway collapse and obstruction. As used herein, the term, "protruded state" with regard to the tongue refers to a position that is moved forward and/or downward compared to the non-stimulated position or a relaxed position. Those of skill in the art will recognize that to be in a protruded state does not require the tongue to be coming out of the mouth of the patient, indeed it is preferable that the tongue not extend out of the mouth of the patient, but only be advanced forward to a point where obstruction of the airway is mitigated or eliminated. The protruded state is a state associated with the recruitment of protrusor muscles of the tongue (also sometimes referred to as "protruder" muscles of the tongue) including the genioglossus and geniohyoid muscles. A protruded state is the opposite of a retracted and/or elevated position associated with the recruitment of the retractor muscles, e.g., styloglossus and hyoglossus muscles, which retract and elevate the tongue. Electrical stimulation is delivered to cause the tongue to move to and maintain a protruded state to prevent collapse, open or widen the upper airway of a patient to promote unrestricted or at least reduced restriction of airflow during breathing.

OSA is known to be position dependent in many subjects when sleeping. The supine (face up) position is most commonly associated with anterior/posterior collapse of the airway where the tongue falls back against the posterior aspect of the retro-lingual airway thus closing of the airflow path between the mouth/nose and lungs. Conversely, the prone (face down) position is least associated with OSA with other sleeping positions being more/less common for OSA occurrence dependent on the individual subject.

One aspect of the disclosure is directed to the use of a sensor such as an accelerometer to determine the patient's posture. Once the patient's posture is determined, a control circuit in the INS can initiate electrical stimulation to the patient's lingual muscles to prevent airway collapse when the subject is in sleeping positions known to be prone to having airway collapse.

Subjects who have OSA and are candidates for neurostimulation will typically undergo an assessment of their proneness to airway collapse based on sleeping position during their initial meetings with medical professionals or during a sleep study. Those with a high correlation of OSA to sleeping position will benefit from having their INS programmed to become active when the subject is in the position(s) that have a high correlation. Similarly, the INS may be programmed to become inactive or less active when there is little or low correlation of position to incidence of OSA, thus reducing the potential for fatigue of the protrusor muscles by application of unnecessary therapy. A sensor in the INS will sense position of the patient and respond with a pre-programmed simulation pattern to prevent OSA as defined by the surgical and assessment team, when it is determined the patient is in a position in need of therapy application.

FIG. 1 is a conceptual diagram of an implantable neurostimulator (INS) system for delivering OSA therapy. The INS system 10 includes at least one electrical lead 20 and a pulse generator 12. Pulse generator 12 includes a housing 15 enclosing circuitry including a control circuit, therapy delivery circuit, optional sensor, a battery, and telemetry circuit as described below in conjunction with FIG. 2. A connector assembly 17 is hermetically sealed to housing 15 and includes one or more connector bores for receiving at least one medical electrical lead used for delivering OSA therapy and, in some examples, for sensing physiological conditions such as electromyogram (EMG) signals and the like. As depicted in FIG. 1 the pulse generator 12 is implanted in the neck of the patient 8. The instant disclosure is not so limited, and the pulse generator 12 may be located in other locations such as in the chest area or other areas known to those of skill in the art.

Lead 20 includes a flexible, elongate lead body 22 that extends from a lead proximal end 24 to a lead distal end 26. At least two electrodes 30 are carried along a lead distal portion adjacent lead distal end 26 that are configured for insertion within the protrusor muscles 42a, 42b and 46 of the patient's tongue 40. The electrodes 30 are configured for implantation within soft tissue such as musculature proximate to the medial branches of one or both hypoglossal nerves (HGN) that innervate the protrusor muscles of the tongue. The electrodes may be placed approximately 5 mm (e.g., from 2 mm to 8 mm) from a major trunk of the HGN. As such, the electrodes 30 may be referred to herein as "intramuscular electrodes," in contrast to an electrode that is placed on or along a nerve trunk or branch, such as a cuff electrode, used to directly stimulate the nerve trunk or branch. Lead 20 may be referred to herein as an "intramuscular lead" since the lead distal end and electrodes 30 are configured for advancement through the soft tissue, which may include the protrusor muscle tissue, to anchor electrodes 30 in proximity of the HGN branches that innervate the protrusor muscles 42a, 42b and 46. The term "intramuscular" with regard to electrodes 30 and lead 20 is not intended to be limiting, however, since the electrodes 30 may be implanted in connective tissue or other soft tissue proximate the medial HGN and its branches. One or more electrodes 30 may be placed in an area of protrusor muscles 42a, 42b and 46 that include motor points, where each nerve axon terminates in the muscle (also called the neuro-muscular junction). The motor points are not at one location but spread out in the protrusor muscles. Leads 20 may be implanted such that one or more electrodes 30 may be generally in the area of the motor points (e.g., such that the motor points are within 1 to 10 mm from one or more electrodes 30).

The protrusor muscles are activated by electrical stimulation pulses generated by pulse generator 12 and delivered via the intramuscular electrodes 30 to move tongue 40 forward, to promote a reduction in obstruction or narrowing of the upper airway 6 during sleep. As used herein, the term "activated" with regard to the electrical stimulation of the protrusor muscles refers to electrical situation that causes depolarization or an action potential of the cells of the nerve (e.g., hypoglossal nerve(s)) innervating the protrusor muscles and motor points and subsequent depolarization and mechanical contraction of the protrusor muscle cells. In some cases, the muscles may be activated directly by the electrical stimulation pulses. The protrusor muscles that may be activated by stimulation via intramuscular electrodes 30 may include at least one or both of the right and/or left genioglossus muscle (GG) 42, which includes the oblique compartment (GGo) 42a and the horizontal compartment (GGh) 42b (referred to collectively as GG 42) and/or the right and/or left geniohyoid muscle (GH) 46. The GG muscle and GH muscle are innervated by a medial branch of the HGN (also referred to as the XII$^{th}$ cranial nerve), while the hyoglossus and styloglossus muscles, which cause retraction and elevation of the tongue, are innervated by a lateral branch of the HGN.

The multiple distal electrodes 30 may be used to deliver bilateral or unilateral stimulation to the GG 42 and/or the GH 46 muscles via the medial branch of the HGN or branches thereof, also referred to herein as the "medial HGN." Distal electrodes 30 may be switchably coupled to output circuitry of pulse generator 12 to enable delivery of electrical stimulation pulses in a manner that selectively activates the right and left protrusor muscles in a cyclical or alternating pattern to avoid muscle fatigue while maintaining upper airway patency. Additionally or alternatively, electrical stimulation may be delivered to selectively activate the GG 42 and/or GH 46 muscles or portions thereof during unilateral stimulation of the left or right protrusor muscles.

The lead proximal end 24 includes a connector (not shown in FIG. 1) that is couplable to connector assembly 17 of pulse generator 12 to provide electrical connection between circuitry enclosed by the housing 15 of pulse generator 12, e.g., including therapy delivery circuitry and control circuitry as described below in conjunction with FIG. 2. The lead body 22 encloses electrical conductors extending from each of the distal electrodes 30 to the proximal connector at proximal end 24 to provide electrical connection between output circuitry of pulse generator 12 and the electrodes 30.

Figure 2:
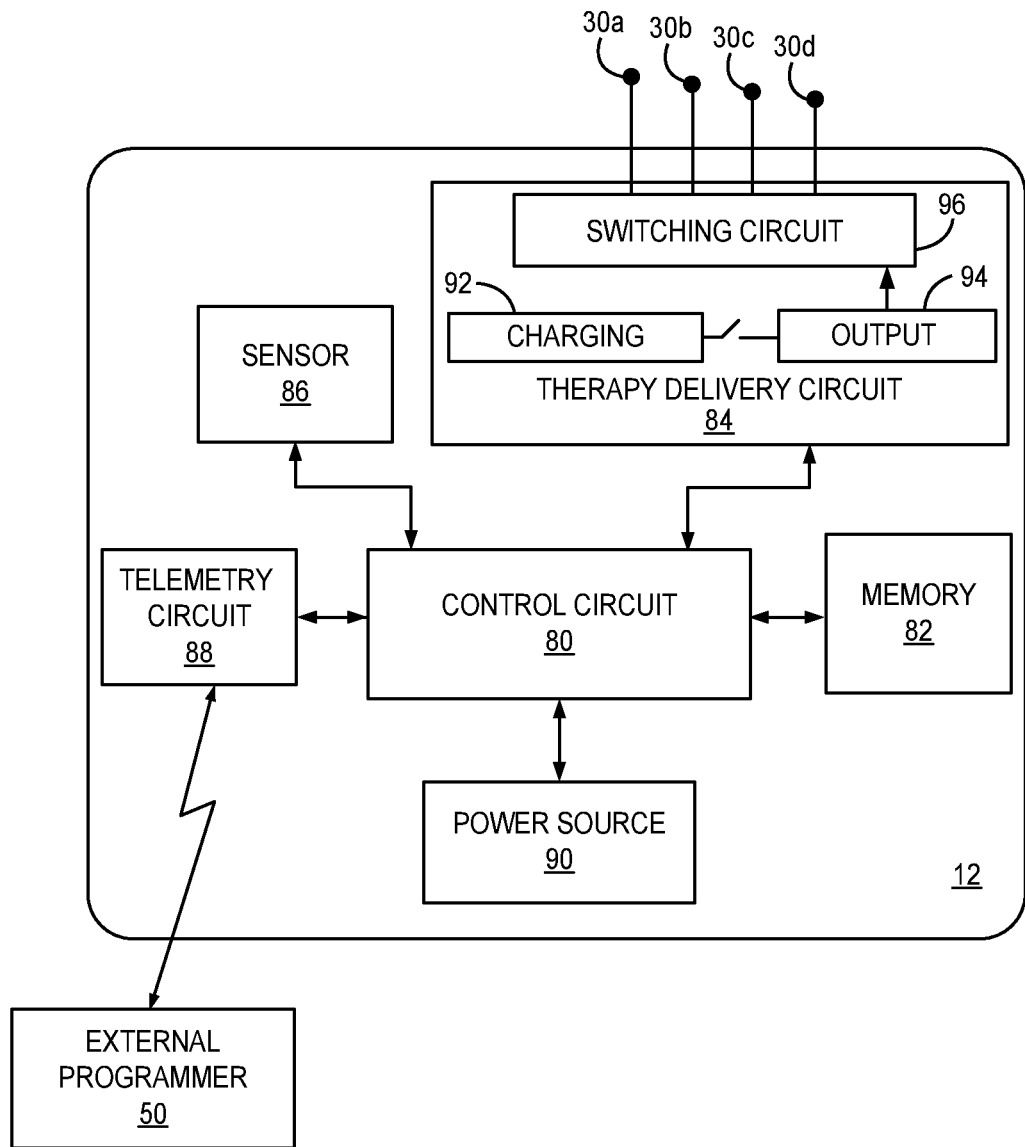
FIG. 2 is a conceptual diagram of a pulse generator included in INS of FIG. 1.

FIG. 2 is a schematic diagram of pulse generator 12. Pulse generator 12 includes a control circuit 80, memory 82, therapy delivery circuit 84, a sensor 86, telemetry circuit 88 and power source 90. Power source 90 may include one or more rechargeable or non-rechargeable batteries for supplying electrical current to each of the control circuit 80, memory 82, therapy delivery circuit 84, sensor 86 and telemetry circuit 88. While power source 90 is shown in communication only with control circuit 80 for the sake of clarity, it is to be understood that power source 90 provides power as needed to each of the circuits and components of pulse generator 12 as needed. For example, power source 90 provides power to therapy delivery circuit 84 for generating electrical stimulation pulses.

The functional blocks shown in FIG. 2 represent functionality included in a pulse generator configured to delivery an OSA therapy and may include any discrete and/or integrated electronic circuit components that implement analog and/or digital circuits capable of producing the functions attributed to a pulse generator herein. The various components may include an application specific integrated circuit (ASIC), an electronic circuit, a processor (shared, dedicated, or group) and memory that execute one or more software or firmware programs, a combinational logic circuit, state machine, or other suitable components or combinations of components that provide the described functionality. Providing software, hardware, and/or firmware to accomplish the described functionality in the context of any modern cardiac medical device system, given the disclosure herein, is within the abilities of one of skill in the art.

Control circuit 80 communicates, e.g., via a data bus, with memory 82, therapy delivery circuit 84, telemetry circuit 88 and sensor 86 (when included) to control OSA therapy delivery and other pulse generator functions. As disclosed herein, control circuit 80 may pass control signals to therapy delivery circuit 84 to cause therapy delivery circuit 84 to deliver electrical stimulation pulses via electrodes 30 according to a therapy protocol that may include selective stimulation patterns of right and left portions of the GG and GH muscles and/or proximal and distal portions of the GG and GH muscles. Control circuit 80 may further be configured to pass therapy control signals to therapy delivery circuit 84 including stimulation pulse amplitude, stimulation pulse width, stimulation pulse number and frequency of a stimulation pulse train.

Memory 82 may store instructions for execution by a processor included in control circuit 80, stimulation control parameters, and other device-related or patient-related data. Control circuit 80 may retrieve therapy delivery control parameters and a therapy delivery protocol from memory 82 to enable control circuit 80 to pass control signals to therapy delivery circuit 84 for controlling the OSA therapy. Memory 82 may store historical data relating to therapy delivery for retrieval by a user via telemetry circuit 88. Therapy delivery data or information stored in memory 82 may include therapy control parameters used to deliver stimulation pulses as well as delivered therapy protocol(s), hours of therapy delivery or the like. When sensor 86 is included, patient related data determined from a sensor signal may be stored in memory 82 for retrieval by a user.

Therapy delivery circuit 84 may include a charging circuit 92, an output circuit 94, and a switching circuit 96. Charging circuit 92 may include one or more holding capacitors that are charged using a multiple of the battery voltage of power source 90, for example. The holding capacitors are switchably connected to output circuit 94, which may include one or more output capacitors that are coupled to a selected bipolar electrode pair via switching circuit 96. The holding capacitor(s) are charged to a programmed pacing pulse voltage amplitude by charging circuit 92 and discharged across the output capacitor for a programmed pulse width. Charging circuit 92 may include capacitor charge pumps or an amplifier for the charge source to enable rapid recharging of holding capacitors included in charging circuit 92. Therapy delivery circuit 84 responds to control signals from control circuit 80 for generating and delivering trains of pulses to produce sustained tetanic contraction of the GG and/or GH muscles or portions thereof to move the tongue forward and avoid upper airway obstruction.

Output circuit 94 may be selectively coupled to bipolar pairs of electrodes 30a-30d via switching circuit 96. Switching circuit 96 may include one or more switches activated by timing signals received from control circuit 80. Electrodes 30a-30d may be selectively coupled to output circuit 94 in a time-varying manner to deliver stimulation to different portions of the protrusor muscles at different time to avoid fatigue, without requiring stimulation to be withheld completely. Switching circuit 96 may include a switch array, switch matrix, multiplexer, or any other type of switching device(s) suitable to selectively couple therapy delivery circuit 84 to bipolar electrode pairs selected from electrodes 30. Bipolar electrode pairs may be selected one at a time or may be selected two or more at time to allow overlapping stimulation of two or more different portions of the protrusor muscles. Overlapping stimulation times of two portions of the protrusor muscles, for example left and right or proximal and distal may maintain a forward position of the tongue and allow a ramping up and ramping down of the electrical stimulation being delivered to two different portions of the protrusor muscles.

Telemetry circuit 88 is optional but may be included to enable bidirectional communication with an external programmer 50. A user, such as the patient 8, may manually adjust therapy control parameter settings, e.g., as described in Medtronic's Patient Programmer Model 37642, incorporated by reference in its entirety. The patient may make limited programming changes such as small changes in stimulation pulse amplitude and pulse width. The patient may turn the therapy on and off or to set timers to turn the therapy on or off using external programmer 50 in wireless telemetric communication with telemetry circuit 88.

In other examples, a user, such as a clinician, may interacts with a user interface of an external programmer 50 to program pulse generator 12 according to a desired OSA therapy protocol. For example, a Physician Programmer Model 8840 available from Medtronic, Inc., Minneapolis, Minn., may be used by the physician to program pulse generator 12 for delivering electrical stimulation.

Programming of pulse generator 12 may refer generally to the generation and transfer of commands, programs, or other information to control the operation of pulse generator 12. For example, external programmer 50 may transmit programs, parameter adjustments, program selections, group selections, or other information to control the operation of pulse generator 12, e.g., by wireless telemetry. As one example, external programmer 50 may transmit parameter adjustments to support therapy changes. As another example, a user may select programs or program groups. A program may be characterized by an electrode combination, electrode polarities, voltage or current amplitude, pulse width, pulse rate, therapy duration, and/or pattern of electrode selection for delivering patterns of alternating portions of the protrusor muscles that are being stimulated. A group may be characterized by multiple programs that are delivered simultaneously or on an interleaved or rotating basis. These programs may adjust output parameters or turn the therapy on or off at different time intervals.

In some cases, external programmer 50 may be characterized as a physician or clinician programmer if it is primarily intended for use by a physician or clinician. In other cases, external programmer 50 may be characterized as a patient programmer if it is primarily intended for use by a patient. A patient programmer 50 is generally accessible to patient 12 and, in many cases, may be a portable device that may accompany the patient throughout the patient's daily routine. In general, a physician or clinician programmer may support selection and generation of programs by a clinician for use by pulse generator 12, whereas a patient programmer may support adjustment and selection of such programs by a patient during ordinary use.

External programmer 50 may present patient related and/or device related data retrieved from memory 82 via telemetry circuit 88. Additionally or alternatively external programmer 50 may present sleep sound or motion data stored in memory 82 as determined from signals from sensor 86. As explained in greater detail below, the time periods in which the patient is lying down can be acquired based on patient posture detection using sensor 86 and a history of such data can be stored into memory 82 and retrieved and displayed by external programmer 50.

Figure 3:
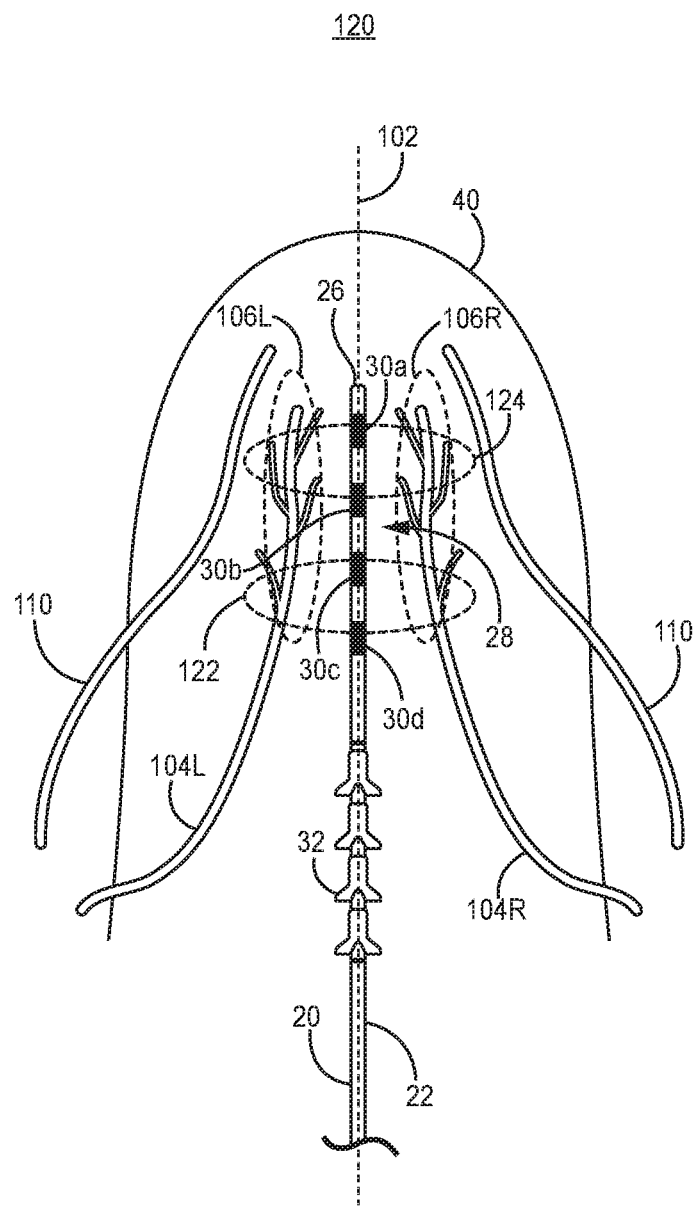
FIG. 3 is a diagram of the distal portion of the lead of FIG. 1 deployed for delivering OSA therapy according to one aspect of the disclosure.

FIG. 3 depicts a single intramuscular lead 20 inserted into the tongue 40 of a patient. Lead 20 may include two or more electrodes, and in the example shown lead 20 includes four electrodes 30a, 30b, 30c, and 30d (collectively referred to as "electrodes 30") spaced apart longitudinally along lead body 22. Lead body 22 is a flexible lead body which may define one or more lumens within which insulated electrical conductors extend to a respective electrode 30a-30d. The distal most electrode 30a may be adjacent or proximate to lead distal end 26. Each of electrodes 30b, 30c and 30d are spaced proximally from the respective adjacent electrode 30a, 30b and 30c by a respective interelectrode distance.

Each electrode 30a-30d is shown have equivalent electrode lengths. In other examples, however, electrodes 30a-30d may have electrode lengths that are different from each other in order to optimize placement of the electrodes 30 or the resulting electrical field of stimulation relative to targeted stimulation sites corresponding to left and right portions of the HGN or branches thereof and/or motor points of the GG and GH muscles. The interelectrode spacings between electrodes 30a, 30b, 30c, and 30d are shown to be approximately equal in FIG. 3, however they may also be different from each other in order to optimize placement of electrodes 30 relative to the targeted stimulation sites or the resulting electrical field of stimulation relative to targeted stimulation sites corresponding to left and right hypoglossal nerves or branches of hypoglossal nerves and/or motor points of protrusor muscles 42a, 42, or 46.

In some examples, electrodes 30a and 30b form an anode and cathode pair for delivering bipolar stimulation in one portion of the protrusor muscles, e.g., either the left or right GG and/or GH muscles or either a proximal or distal portion of the GG and/or GH muscles. Electrodes 30c and 30d may form a second anode and cathode pair for delivering bipolar stimulation in a different portion of the protrusor muscles (e.g., the other of the left or right portions or the other of the proximal or distal portions). Accordingly, the interelectrode spacing between the two bipolar pairs 30a-30b and 30c-30d may be different than the interelectrode spacing and between the anode and cathode within each bipolar pair 30a-30b and 30c-30d.

In one example, the total distance encompassed by electrodes 30a-30d along the lead body 22 may be about 20 millimeter, 25 millimeters, or 30 millimeters as examples. In one example, the total distance is between 20 and 22 millimeters. The interelectrode spacings between a proximal electrode pair 30c-30d and a distal electrode pair 30a-30b, respectively, may be between 2 and 6 mm, including all integer values therebetween. The interelectrode spacing separating the distal and proximal pairs 30a-30b and 30c-

30d may be the same or different from each other and the spacing between individual electrodes of any such pair.

In the example shown, each of electrodes 30a-30d is shown as a circumferential ring electrode which may be uniform in diameter with lead body 22. In other examples, electrodes 30 may include other types of electrodes such as a tip electrode, a helical electrode, a coil electrode, a segmented electrode, a button electrode as examples. For instance, the distal most electrode 30a may be provided as a tip electrode at the lead distal end 26 with the remaining three electrodes 30b, 30c and 30d being ring electrodes. When electrode 30a is positioned at the distal end 26, electrode 30a may be a helical electrode configured to screw into the muscle tissue at the implant site to additionally serve as a fixation member for anchoring the lead 20 at the targeted therapy delivery site. In other examples, one or more of electrodes 30a-d may be a hook electrode or barbed electrode to provide active fixation of the lead 20 at the therapy delivery site.

Lead 20 may include one or more fixation member 32 for minimizing the likelihood of lead migration. In the example shown, fixation member 32 includes multiple sets of tines which engage the surrounding tissue when lead 20 is positioned at the target therapy delivery site. The tines of fixation member 32 may extend radially and proximally at an angle relative to the longitudinal axis of lead body 22 to prevent or reduce retraction of lead body 22 in the proximal direction. Tines of fixation member 32 may be collapsible against lead body 22 when lead 20 is held within the confines of a lead delivery tool, e.g., a needle or introducer, used to deploy lead 20 at the target implant site. Upon removal of the lead delivery tool, the tines of fixation member 32 may spread to a normally extended position to engage with surrounding tissue and resist proximal and lateral migration of lead body 22. In other examples, fixation member 32 may include one or more hooks, barbs, helices, or other fixation mechanisms extending from one or more longitudinal locations along lead body 22 and/or lead distal end 26. Fixation member 32 may partially or wholly engage the GG, GH muscles and/or other muscles below the tongue, and/or other soft tissues of the neck, e.g., fat and connective tissue, when proximal end of lead body 20 is tunneled to an implant pocket of pulse generator 12. In other examples, fixation member 32 may include one or more fixation mechanisms located at other locations than the location shown in FIG. 3, including at or proximate to distal end 26, between electrodes 30, or otherwise more distally or more proximally than the location shown. The implant pocket of pulse generator 12 may be along the patient's neck 8 (see FIG. 1). Accordingly the length of the elongated lead body 22 from distal end 26 to the lead proximal end 24 (FIG. 1) may be selected to extend from the a target therapy delivery site in the protrusor muscles to a location along the patient's neck where the pulse generator 12 is implanted. This length may be up to 10 cm or up to 20 cm as examples but may generally be 25 cm or less, though longer or shorter lead body lengths may be used depending on the anatomy and size of the individual patient.

FIG. 3 further depicts the lead 20 deployed for delivering OSA therapy according to another example. In this example, lead 20 carrying electrodes 30 is advanced approximately along or parallel to midline 102 of tongue 40. In the example shown, lead body 22 is shown approximately centered along midline 102, however in other examples lead body 22 may be laterally offset from midline 102 in the left or right directions but is generally medial to both of the left HGN 104L and the right HGN 104R. The distal end 26 of lead 20 may be inserted inferiorly to the body of tongue 40, e.g., at a percutaneous insertion point along the submandibular triangle, in the musculature below the floor of the oral cavity. The distal end 26 is advanced to position electrodes 30 medially to the left and right HGNs 104L and 104R, e.g., approximately midway between the hyoid bone the mental protuberance (chin). An electrical field produced by stimulation pulses delivered between any bipolar pair of electrodes selected from electrodes 30 may encompass a portion of both the left target region 106L and the right target region 106R to produce bilateral stimulation of the HGNs 104L and 104R and therefore bilateral recruitment of the protrusor muscles. Bilateral recruitment of the protrusor muscles may provide greater airway opening than unilateral stimulation that is generally performed using a nerve cuff electrode along the HGN. For example, electrical stimulation pulses delivered using electrodes 30a and 30b may produce electrical field 122 (shown conceptually) encompassing a portion of both of the left and right target regions 106L and 106R. Electrical stimulation pulses delivered using electrodes 30c and 30d may produce electrical field 124 (shown conceptually) encompassing a portion of both of the left and right target regions 106L and 106R. The portions of the left and right target regions 106L and 106R encompassed by electrical field 122 are posterior portions relative the portions of the left and right target regions 106L and 106R encompassed by electrical field 124.

In some examples, electrical stimulation is delivered by pulse generator 12 by sequentially selecting different electrode pairs from among the available electrodes 30 to sequentially recruit different bilateral anterior and bilateral posterior portions of the HGNs 104L and 104R. This electrode selection may result in recruitment of different anterior and posterior portions of the protrusor muscles. The sequential selection of different electrode pairs may be overlapping or non-overlapping. The electrical stimulation is delivered throughout an extended time period encompassing multiple respiratory cycles independent of the timing of respiratory cycles to maintain a protruded state of tongue 40 from the beginning of the time period to the end of the time period. The electrodes 30 may be selected in bipolar pairs comprising the most distal pair 30a and 30b, the outermost pair 30a and 30d, the innermost pair 30b and 30c, the most proximal pair 30c and 30d or alternating electrodes along lead body 22, e.g., 30a and 30c or 30b and 30d. Sequential selection of two or more different electrode pairs allows for sequential recruitment of different portions of the protrusor muscles to reduce the likelihood of fatigue.

In some examples, electrical stimulation delivered using an electrode pair, e.g., 30a and 30b, that is relatively more distal along distal lead portion 28 and implanted relatively anteriorly along tongue 40 may recruit a greater portion of anterior muscle fibers, e.g., within the GG muscle. Electrical stimulation delivered using an electrode pair, e.g., 30c and 30d, that is relatively more proximal along distal lead portion 28 and implanted relatively posteriorly along tongue 40 may recruit a greater portion of posterior muscle fibers, e.g., within the GH muscle. Sequential selection of electrodes 30 for delivering electrical stimulation pulses allows sequential recruitment in overlapping or non-overlapping patterns of anterior and posterior portions of the protrusor muscles to sustain the tongue in a protruded state throughout the extended time period while reducing or avoiding muscle fatigue.

Figure 4:
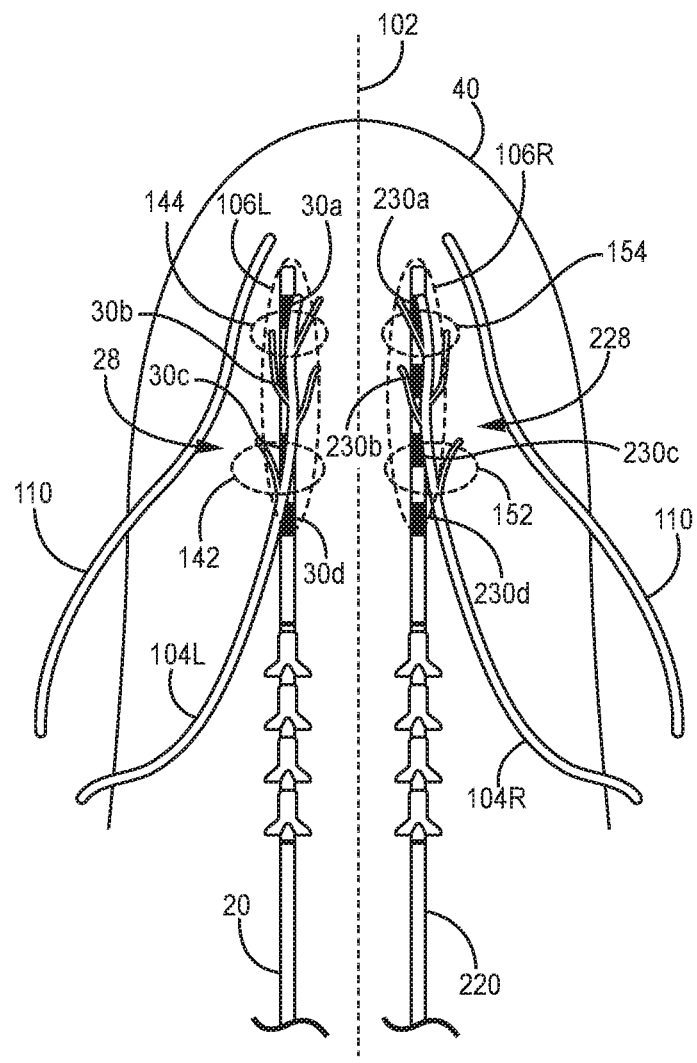
FIG. 4 is a diagram of the distal portion of a two lead INS deployed for delivering OSA therapy according to a further aspect of the disclosure.

FIG. 4 depicts the distal portion of a dual lead system for delivering OSA therapy. In this example, one lead 20 is advanced anteriorly approximately parallel to midline 102 and offset, e.g. by 5-8 millimeters to the left of midline 102, to position distal portion 28 and electrodes 30 in or adjacent to the left target region 106L. A second lead 220 is advanced anteriorly approximately parallel to midline 102 but offset laterally to the right of midline 102 to position distal portion 228 and electrodes 230 in or adjacent the right target region 106R. Lead 20 may be inserted from a left lateral or posterior approach of the body of tongue 40, and lead 230 may be inserted from a right lateral or posterior approach of the body of tongue 40. In other examples, both leads 20 and 220 may be inserted from only a left or only a right approach with one lead traversing midline 102 to position the electrodes 30 or 230 along the opposite side of midline 102 from the approaching side. Lead 20 and/or lead 220 may be advanced at an oblique angle relative to midline 102 but may not cross midline 102. In other examples, one or both leads 20 and 220 may approach and cross midline 102 at an oblique angle such that one or both of distal portions 28 and 228 extend in or adjacent to both the right and left target regions 106L and 106R.

In the example shown, relatively more localized control of the recruitment of left, right, anterior and posterior portions of the protrusor muscles may be achieve by selecting different electrode pairs from among the electrodes 30a through 30d and 230a through 230d. For example, any combination of electrodes 30a through 30d may be selected for delivering electrical stimulation pulses to the left portions of the protrusor muscles. More distal electrodes 30a and 30b may be selected for stimulation of more anterior portions of the left protrusor muscles (corresponding to electrical field 144) and more proximal electrodes 30c and 30d may be selected for stimulation of more posterior portions of the left protrusor muscles (corresponding to electrical field 142). Any combination of electrodes 230a through 230d may be selected for delivering electrical stimulation pulses to the right portions of the protrusor muscles. More distal electrodes 230a and 230b may be selected for stimulation of more anterior portions of the right protrusor muscles (corresponding to electrical field 154) and more proximal electrodes 230c and 230d may be selected for stimulation of more posterior portions of the right protrusor muscles (corresponding to electrical field 152).

Switching circuit 96 may be configured to select electrode pairs that include one electrode on one of leads 20 or 220 and another electrode on the other lead 20 or 220 to produce an electrical field (not shown) that encompasses portions of both the left target region 106L and the right target region 106R simultaneously for bilateral stimulation. Any combination of the available electrodes 30a through 30d and electrodes 230a through 230d may be selected as two or more bipolar pairs, which are selected in a repeated, sequential pattern to sequentially recruit different portions of the two target regions 106L and 106R. The sequential selection of electrode pairs may be overlapping or non-overlapping, but electrical stimulation pulses are delivered without interruption at one or more selected frequencies throughout an extended time period to maintain tongue 40 in a protruded state from the beginning of the time period to the end of the time period, encompassing multiple respiratory cycles.

In the example of FIG. 4 including two leads, two pairs of electrodes may be selected simultaneously and sequentially with one or more other pairs of electrodes. For example, electrodes 30a and 30b may be selected as one bipolar pair and electrodes 230c and 230d may be selected as a second bipolar pair for simultaneous stimulation of the left, anterior portion of the target region 106L and the right posterior portion of the target region 106R. The electrodes 30c and 30d may be selected as the next bipolar pair from lead 20, simultaneously with electrodes 230a and 230b selected as the next bipolar pair from lead 220. In this way, electrical stimulation may be delivered bilaterally, alternating between posterior and anterior regions on each side. The anterior left (30a and 30b) and posterior right (230c and 230d) bipolar pairs may be selected first, and the posterior left (30c and 30d) and anterior right (230a and 230b) bipolar pairs may be selected second in a repeated, alternating fashion to maintain tongue 40 in a protruded state continuously during an extended time period encompassing multiple respiratory cycles. In other examples, both of the anterior pairs (30a-30b and 230a-230b) may be selected simultaneously first, and both the posterior pairs (30c-30d and 230c-230d) may be selected simultaneously second, sequentially following the anterior pairs. In this way, continuous bilateral stimulation may be achieved while sequentially alternating between posterior and anterior portions to avoid or reduce fatigue. In contrast to other OSA therapy systems that rely on a sensor for sensing the inspiratory phase of respiration to coordinate the therapy with the inspiratory phase, the intramuscular electrodes 30 positioned to stimulate different portions of the protrusor muscles do not require synchronization to the respiratory cycle. Alternation of stimulation locations within the protrusor muscles allows different portions of the muscles to rest while other portions are activated to avoid collapse of the tongue against the upper airway while also avoiding muscle fatigue.

It is to be understood that more or fewer than the four electrodes shown in the examples presented herein may be included along the distal portion of a lead used in conjunction with the OSA therapy techniques disclosed herein. A lead carrying multiple electrodes for delivering OSA therapy may include 2, 3, 5, 6 or other selected number of electrodes. When the lead includes only two electrodes, a second lead having at least one electrode may be included to provide at least two different bipolar electrode pairs for sequential stimulation of different portions of the right and/or left medial HGNs. Furthermore, while the selected electrode pairs are generally referred to herein as "bipolar pair" including one cathode and one return anode, it is recognized that three or more electrodes may be selected at a time to provide desired electrical field or stimulation vector for recruiting a desired portion of the protrusor muscles. Accordingly the cathode of a bipolar "pair" may include one or more electrodes selected simultaneously from the available electrodes and/or the anode of the bipolar "pair" may include one or more electrodes selected simultaneously from the available electrodes.

Figure 5:
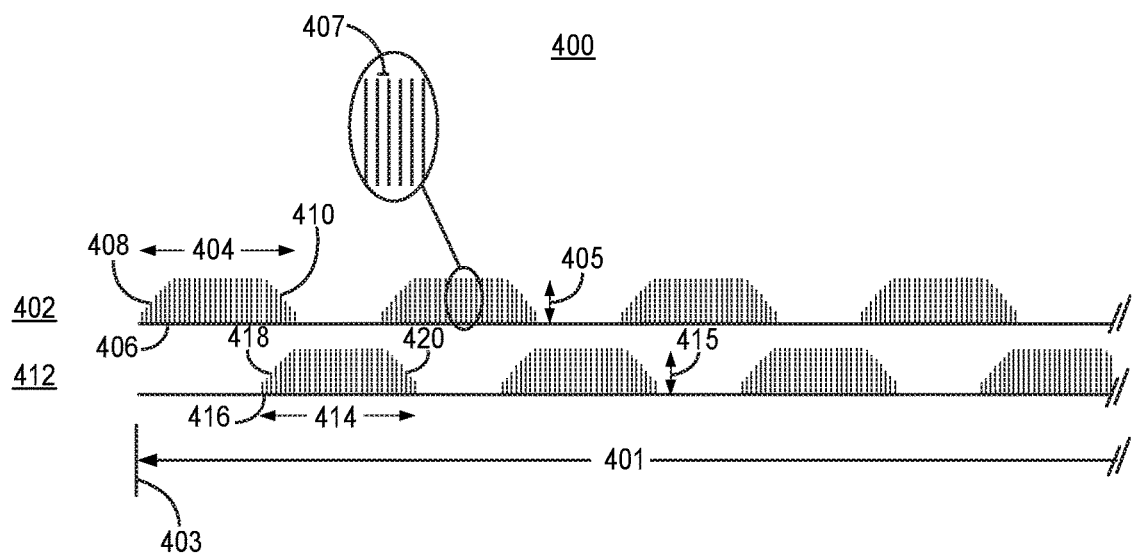
FIG. 5 timing diagram illustrating a method performed by the system of FIG. 1 for delivering selective stimulation to the protrusor muscles for promoting upper airway patency during sleep according to one example.

FIG. 5 timing diagram illustrating a method performed by pulse generator 12 for delivering selective stimulation to the protrusor muscles for promoting upper airway patency during sleep according to one example. Electrical stimulation is delivered over a therapy time period 401 having a starting time 403 and an ending time (not shown). Electrical stimulation pulses that are delivered when pulse generator sequentially selects a first bipolar electrode pair 402 and a second bipolar electrode pair 412 in an alternating, repeating manner are shown. The first and second bipolar electrode pairs 402 and 412 may correspond to any two different electrode pairs described in the examples above in conjunction with FIGS. 3-4.

A first train of electrical pulses 406 is shown starting at the onset 403 or therapy time period 401. The first train of electrical pulses 406 is delivered using bipolar electrode pair 402 for a duty cycle time interval 404. The first train of electrical pulses 406 has a pulse amplitude 405 and pulse frequency, e.g., 20 to 50 Hz, defined by the interpulse intervals 407. The first train of electrical pulses 406, also referred to as "pulse train" 406, may have a ramp on portion 408 during which the pulse amplitude is gradually increased from a starting voltage amplitude up to pulse voltage amplitude 405. In other examples, the pulse width may be gradually increased. In this way the delivered pulse energy is gradually increased to promote a gentle transition from the relaxed, non-stimulated state to the protruded state of the tongue.

The train of electrical pulses 406 may include a ramp off portion 410 during which the pulse amplitude (and/or pulse width) is decremented from the pulse voltage amplitude 405 to an ending amplitude at the expiration of the duty cycle time interval 404. In other examples, pulse train 406 may include a ramp on portion 408 and no ramp off portion 410. In this case, the last pulse of pulse train 406 delivered at the expiration of duty cycle time interval 404 may be delivered at the full pulse voltage amplitude 405. Upon expiration of the duty cycle time interval 404, electrical stimulation delivery via bipolar electrode pair 402 is terminated.

In the example shown, a second electrode pair 412 is selected when of duty cycle time interval 404 is expiring. The second electrode pair 412 may be selected such that delivery of electrical stimulation pulse train 416 starts a ramp on portion 418 that is simultaneous with the ramp of portion 410 of train 406. In other examples, the ramp on portion 418 of pulse train 416 may start at the expiration of the first duty cycle time interval 404. When pulse train 406 does not include a ramp off portion 410, the pulse train 416 may be started such that the ramp on portion 418 ends just before, just after or coincidentally with the expiration of duty cycle time interval 404. The second pulse train 416 has a duration of duty cycle time interval 414 and may end with an optional ramp off portion 420, which may overlap with the ramp on portion of the next pulse train delivered using the first electrode pair 402.

In this example, pulse trains 406 and 416 are shown to be equivalent in amplitude 405 and 415, pulse width, pulse frequency (and inter pulse interval 407), and duty cycle time interval 404 and 414. It is contemplated, however, that each of the stimulation control parameters used to control delivery of the sequential pulse trains 406 and 416 may be separately controlled and set to different values as needed to achieve a desired sustained protrusion of tongue 40 while avoiding or minimizing fatigue.

The sequential pulse trains 406 and 416 are delivered using two different electrode pairs 402 and 412 such that different portions of the protrusor muscles are recruited by the pulse trains 406 and 416 allowing one portion to rest while the other is being stimulated. However, pulse trains 404 and 406 occur in a sequential overlapping or non-overlapping manner such that electrical pulses are delivered at one or more selected frequencies for the entire duration of the therapy time period 401 to sustain the tongue in a protruded state throughout time period 401. It is to be understood that the relative down and/or forward position of the protruded tongue may shift or change as different electrode pairs are selected but the tongue remains in a protruded state throughout therapy time period 401.

At times, the pulse trains 404 and 406 may be overlapping to simultaneously recruit the left and right GG and/or GH muscles to create a relatively greater force (compared to recruitment of a single side) to pull the tongue forward to open an obstructed upper airway. In some cases, the overlapping pulse trains 404 and 406 may cause temporary fatigue of the protrusor muscles along the left or right side but the temporary fatigue may improve the therapy effectiveness to ensure an open upper airway during an apneic episode. Recovery from fatigue will occur between duty cycles and at the end of an apneic episode. Duty cycle lengths may vary between patients depending on the fatigue properties of the individual patient. Control circuit 80 may control the duty cycle on time in a manner that minimizes or avoids fatigue in a closed loop system using a signal from sensor 86, e.g., a motion sensor signal and or EMG signal correlated protrusor muscle contraction force and subsequent fatigue.

Figure 6:
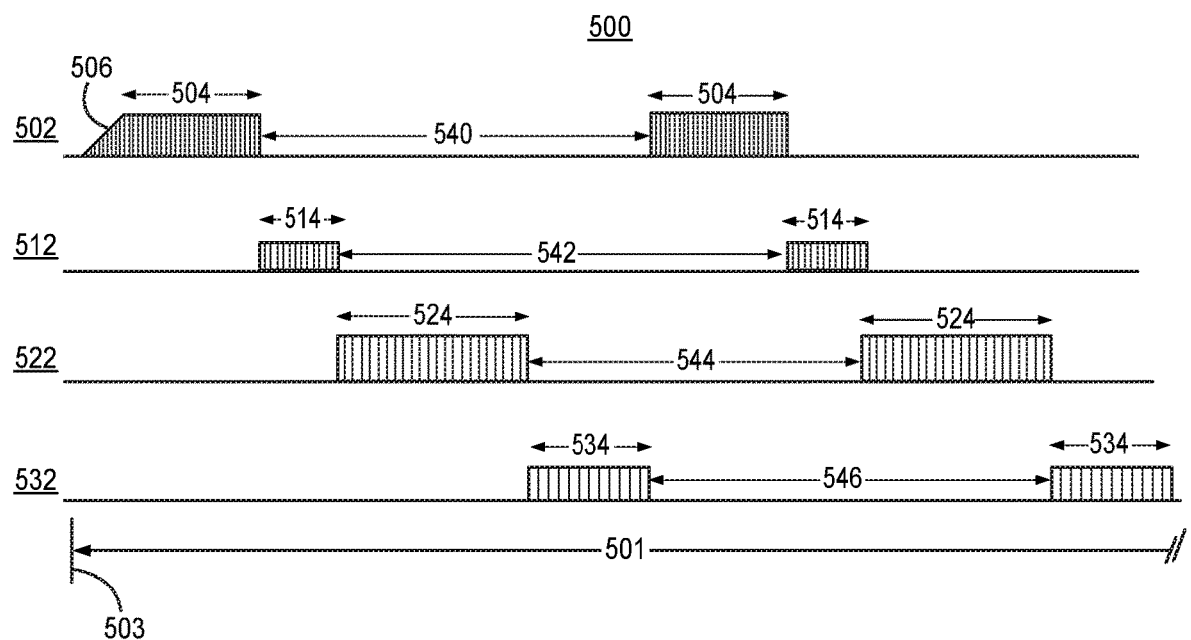
FIG. 6 is a timing diagram of a method for delivering OSA therapy by the system of FIG. 1 according to another example.

FIG. 6 is a timing diagram 500 of a method for delivering OSA therapy by pulse generator 12 according to another example. In this example, a therapy delivery time period 501 is started at 503 with a ramp on interval 506 delivered using a first bipolar electrode pair 502. The ramp on interval 506 is followed by a duty cycle time interval 504. Upon expiration of the duty cycle time interval 504, a second bipolar electrode pair 512 is selected for delivering electrical stimulation pulses for a second duty cycle time interval 514. A third duty cycle time interval 524 starts upon the expiration of the second duty cycle time interval 514, and stimulation pulses are delivered by selecting a third bipolar electrode pair 522 different than the first two pairs 502 and 512. A fourth bipolar pair 532 is selected upon expiration of the third duty cycle time interval 524 and used to deliver stimulation pulses over the fourth duty cycle time interval 534. Upon expiration of the fourth duty cycle time interval 534, the sequence is repeated beginning with duty cycle time interval 504 again.

In this example, four different bipolar pairs are selected in sequence. The four different bipolar electrode pairs may differ by at least one electrode and/or the polarity of another bipolar electrode pair. For example, when a single quadripolar lead 20 is used, the four bipolar pairs may include 30a-30b, 30b-30c, 30c-30d and 30a-30d. The portions of the protrusor muscles recruited by the four different pairs may not be mutually exclusive since the electrical fields of the four different pairs may stimulate some of the same nerve fibers. Four different portions of the protrusor muscles may be recruited, which may include overlapping portions. The relatively long recovery periods 540, 542, 544 and 546 between respective duty cycle time intervals allows each different portion of the protrusor muscles to recover before the next duty cycle. When recruited muscle portions overlap between selected electrode pairs, the bipolar electrode pairs may be selected in a sequence that avoids stimulating the overlapping recruited muscle portions consecutively. All recruited muscle portions are allowed to recover during at least a portion of each respective recovery period 540, 542, 544 and/or 546. For example, if the bipolar electrode pair 502 and the bipolar electrode pair 522 recruit overlapping portions of the protrusor muscles, the recruited portions may still recover during the second duty cycle time interval 514 and during the fourth duty cycle time interval 534.

The duration of each duty cycle time interval, 504, 514, 524 and 534, may be the same or different from each other, resulting in the same or different overall duty cycles. For example, when four bipolar electrode pairs are sequentially selected, stimulation delivery for each individual pair may be a 25% duty cycle. In other examples, a combination of different duty cycles, e.g., 30%, 10%, 40% and 20%, could be selected in order to promote sustained protrusion of the tongue with adequate airway opening while minimizing or avoiding fatigue. The selection of duty cycle may depend on the particular muscles or muscle portions being recruited and the associated response (position) of the tongue to the stimulation for a given electrode pair selection.

The stimulation control parameters used during each of the duty cycle time intervals 504, 514, 524, and 534 for delivering electrical pulses using each of the different bipolar electrode pairs 502, 512, 522 and 532 may be the same or different. As shown, a different pulse voltage amplitude and a different interpulse interval and resulting pulse train frequency may be used. The pulse amplitude, pulse width, pulse frequency, pulse shape or other pulse control parameters may be controlled according to settings selected for each bipolar electrode pair.

In the example shown, one ramp on portion 506 of the stimulation protocol is shown at the onset of the therapy delivery time period 501. Once the stimulation is ramped up to position the tongue in a protruded position, no other subsequent duty cycle time intervals 504 (other than the first one), 514, 524 and 534 may include or be proceeded by a ramp on portion. In other examples, a ramp on portion may precede each duty cycle time interval (or be included in the duty cycle time interval as shown in FIG. 5) and may overlap with the preceding duty cycle time interval. No ramp off portions are shown in the example of FIG. 6. In other examples, ramp off portions may follow or be included in each duty cycle time interval 504, 514, 524 and 534 and may overlap with the onset of the next duty cycle time interval as shown in FIG. 5. In some examples, only the last duty cycle time interval (not shown in FIG. 6) may include or be immediately followed by a ramp off portion to gently allow the tongue to return to a relaxed position at the end of the therapy delivery time period 501.

Following implantation as depicted in FIGS. 3 and 4 and calibration by the surgeon or other caregiver, the INS 10 is ready for use. In accordance with one aspect of the disclosure, the INS system 10 is manually switched on by the patient as part of their routine prior to sleeping. This may be a function of the external programmer 50, or another similar device that can communicate with the pulse generator 12 via the telemetry circuit 88. A delay period may be programmed into the software or firmware employed by the control circuit 80. The delay period allows the patient a period of time to fall asleep before therapy is begun. The period may be established for the patient based on prior sleep studies and adjusted by the patient as desired via the external programmer 50. Without the delay period, the patient would immediately begin to experience the effects of stimulating the muscles of the tongue, which though not dangerous or painful can be observed and may be considered annoying to experience while awake.

As will be appreciated, manual switching is not always a desirable feature in an implantable device associated with sleeping. In a further aspect of the disclosure, OSA therapy may be started and stopped at scheduled times of day. Control circuit 80 may include a clock for scheduling the time that OSA therapy is started and stopped by therapy delivery circuit 84. Many patients, however, are not as rigorous regarding their schedules as would be desired to make the scheduling most effective. Further, the patient my find themselves at a social gathering or other affair at a time where they are normally scheduled for sleeping. Additionally, or alternatively, the patient may find themselves taking an unscheduled nap in a motor vehicle, plane, or train, and not have an opportunity to initiate or schedule therapy. Since OSA is often co-morbid with heart related diseases any instances of experiencing OSA can have complicating factors affecting the patient's heart. Thus, improved sensing of sleeping conditions and initiation of therapy are desirable.

One aspect of the disclosure is directed to a mechanism of initiating therapy based on a determination of the patient's posture. As noted above sensor 86 may include one or more separate sensors for monitoring a patient condition. These sensors may include one or accelerometers, inertial measurement units (IMU), fiber-Bragg gratings (e.g., shape sensors), optical sensors, acoustic sensors, pulse oximeters, and others without departing from the scope of the disclosure. In one aspect of the disclosure sensor 86 is configured as, among other things, as a patient posture sensor.

To achieve a patient posture sensor, the sensor 86 may be, for example, a three-axis accelerometer. A three-axis accelerometer can be employed to detect when the patient is in a reclined or sleeping position and even whether the patient is laying prone or supine or laying on their right or left sides. The effect of 1 G of gravitational acceleration applied directly along an axis of a stationary accelerometer provides a characteristic output voltage signal having an amplitude that can be referenced or scaled as +1 for angular computation purposes. The effect of 1 G of gravitational acceleration applied in precisely the opposite or negative direction to the sensitive axis provides a characteristic output voltage signal amplitude that is referenced or scaled as −1. If the axis is oriented transverse to the direction of the gravitational force, a bias voltage level output signal should be present, and that voltage signal level is referenced or scaled as 0. The degree to which the axis is oriented away or tilted from the direction of the gravitational force can also be detected by the magnitude and polarity of the output voltage signal level deviating from the bias level scaled to 0 and below the output signal level values scaled to +1 and −1. Other scales may be employed, depending on the signal polarities and ranges employed. The sensor 82 may include its own microprocessor with autocalibration of offset error and drift (possibly caused by temperature variation or other things).

TABLE 1

| Posture | $a_x$ | $a_y$ | $a_z$ |
| --- | --- | --- | --- |
| UP | 0 | +1 | 0 |
| SUPINE | 0 | 0 | +1 |
| PRONE | 0 | 0 | −1 |
| RIGHT | −1 | 0 | 0 |
| LEFT | +1 | 0 | 0 |

Table 1 sets forth the ideal, scaled amplitudes of the output signals, ax, ay, and az, respectively, of a three-axis accelerometer employed in sensor 86 and incorporating into INS 10. (The units in the ideal example would be in gravity or "g"). One axis of the accelerometer ($a_y$) is aligned to earth's gravitational field when the pulse generator 12 is implanted. Thus, when standing upright and remaining still, the amplitude or level of the output signal $a_y$ of three-axis accelerometer should be at +1. In this orientation, the scaled amplitudes of the output signals $a_z$ and $a_x$ of the three-axis accelerometer, respectively, should approach 0.

The scaled amplitude of the output signal $a_z$ of the DC three-axis accelerometer should approach +1 or −1, respectively, when the patient lies still and is either supine or prone on their back or stomach and if the INS 10 is implanted with the z-axis of the three axis accelerometer aligned in a posterior-anterior position. In these positions, the amplitudes of the output signals $a_y$ and $a_x$ of the three-axis accelerometer, respectively, should approach 0. In the same fashion, the patient lying on the right and left sides will orient the sensitive axis of the three-axis accelerometer with earth's gravitational field to develop the scaled amplitude of either −1 or +1 of the output signal $a_x$. The amplitudes of the output signals $a_y$ and $a_z$ of the three-axis accelerometer should approach 0. In these ideal orientations of Table I, there is no rotation of the axes of the INS 10 with respect to earth's gravitational field.

As will be appreciated, the determination described above identifies the pose of the pulse generator 12 and not necessarily the patient in which it is implanted. In practice the INS 10 will rarely if ever be implanted in the patient such that the three axes of the three-axis accelerometer precisely align the idea orientations of Table 1. Accordingly, following implantation of the INS 10, a series of calibration tests can be undertaken during which the patient is alternated from standing to lying, from prone to supine, and from right to left sides. By acquiring a series of such values, the sensor 86 can be calibrated for the implantation, to determine the voltage output values of each of the three axes of the accelerometer in each of the positions. Further, though not described in detail herein, similar analyses may be undertaken to determine when a person is in a slightly reclined position such as when sitting in an airplane seat or other position where a person might expect to sleep and may be need of therapy.

As described above, an individual patient may be assessed to determine whether particular postures are triggers for experiencing OSA, and the severity of the experience in each position. These data can be correlated to a specific a stimulation pattern, such as one depicted in FIGS. 5 and 6, for the patient when they are in such a position. As an example, when the patient is in a supine position, the amplitude and pulse width of the therapy may greater than in other positions. Further, laying on a left or right side may cause the stimulation pattern to stimulate just one side or predominantly one side of a patient's protrusor muscles. Importantly, when the sensor 86 determines that the patient is in the standing position, no stimulation is applied. Accordingly, control circuit 80 may monitor the patient posture signal received from sensor 86 and determining when and whether to start OSA therapy.

As will be appreciated, the sensing of a patient's posture alone might not provide sufficient data alone to initiate therapy. Accordingly, the detection of a patient's posture may be just one factor derived from the sensors 86 and other data to determine when to automatically initiate therapy. As one example, a further accelerometer may be employed to determine whether the patient is in motion. The same or an additional accelerometer may be employed to detect other motions and vibrations of the patient including heartbeat, coughing, and snoring as well as vibrations and sounds of the patient's airways associated with sleep apnea. In accordance with one example, the control circuit 80 collects the data from sensors 86 and determines that the patient's posture is not standing, that the patient is not moving, and that the detected heart rate is within a range that is consistent with sleeping or resting. The control circuit 80 thus concludes that the patient is sleeping and therapy delivery circuit 84 may respond to a sleep detection signal from control circuit 80 by initiating the OSA therapy delivery.

Additionally or alternatively, the sensor 86 may detect a signal that is correlated to the movement of the patient's tongue into and out of a protruded state. This signal may be used to detect adequate protrusion and/or fatigue of the stimulated muscle for use in controlling the duty cycle, pulse amplitude and/or stimulating electrode vector of the electrical stimulation therapy delivered by therapy delivery circuit 84. As an example, the sensor 86 can be configured to detect electromyography (EMG) signals. Electromyography is a technique of evaluating and recording the electrical activity produced by skeletal muscles. An electromyograph detects the electrical potential generated by muscle cells when the cells are electrically or neurologically activated.

In accordance with a further aspect of the disclosure, when a stimulation pulse is not being delivered by an electrodes 30a-30d, the electrodes can be employed to detect the electrical potential of muscles. In other examples, dedicated EMG sensing electrodes may be carried by housing 15 and/or lead body 22 and coupled to sensor 86 for EMG signal monitoring. EMG signal monitoring by control circuit 80 may allow detection of a low tonal state of the GG and/or GH muscles indicating a susceptibility to upper airway collapse. Detection of low tonal state of the protrusor muscles may be a trigger for delivering OSA therapy, particularly if combined with a detection of the pose of the patient indicating that they are in a reclined position. Thus, the EMG signals may be used by control circuit 80 for detecting a sleep state and/or low tonal state of the protrusor muscles for use in controlling therapy delivery circuit 84 for delivering stimulation pulses to cause protrusion of the patient's tongue.

EMG monitoring may further be used in monitoring for fatigue of the stimulated GG and/or GH muscles. If fatigue of the muscles is detected, control circuit 80 may alter to control the duty cycle of electrical stimulation pulse trains delivered by therapy delivery circuit 84 to minimize or avoid fatigue and/or allow adequate fatigue recovery time between duty cycle on times. In this manner, Sensor 86 may be configured to produce a signal that is correlated to protrusor muscle tonal state for use by control circuit 80 for detecting a low tonal state predictive of upper airway obstruction, detecting protrusor muscle fatigue, and/or detecting a protruded state of tongue 40. Therapy delivery circuit 84 may be configured to respond to a detection of the protrusor muscle tonal state by control circuit 80 by adjusting one or more control parameters used to control stimulation pulse delivery.

FIG. 7 provides an exemplary method 700 for the implemented in an INS 10 employing a three-axis accelerometer as a sensor 86 configured as a posture detector in accordance with the disclosure. In an initial step, the INS 10 including sensor 86 must be implanted in a patient at step 702. As referenced above, the sensor 86 will have to be calibrated at step 704 for normalize the sensed positions to the patient and the implantation of the INS 10 and sensor 86. In addition to calibration, a series of rules governing whether and how the sensed posture of the patient will initiate or change the application of therapy must be developed and those rules stored in the memory 82 of the INS 10 at step 706. These rules may identify, among other things, the postures in which therapy is to be initiated, the amplitude, pulse width, frequency, bi-polar pairs, and order of pairs for therapy as well as other parameters of the therapy. These rules may also identify how to change the therapy if the posture changes while therapy is being delivered. Further, the rules may include a timing aspect, in which therapy application is delayed following movement or detection of a posture for therapy delivery until the patient has been detected in that posture for a pre-determined time. The rules may be stored in a look-up table in the memory 82 or other suitable form to enable the control circuit 80 to direct the therapy delivery circuit 84.

Once the rules are stored in the memory, the INS is ready to begin delivering therapy based on the sensed posture of the patient. At step 708 output from the sensor 86 is delivered to the control circuit 80 and a determination of the posture of the patient is made at step 710. Following a determination of the posture of the patient, a determination is made at step 712 regarding whether the INS 10 is already delivering therapy. If the INS is already delivering therapy the process moves to step 714 where a determination is made as to whether the therapy being delivered requires adjustment. If adjustment is needed the process moves to step 716 where the therapy is adjusted. Therapy adjustment can range from stopping delivery altogether because the patient is determined to be awake (e.g., with input from a motion sensor) to changing any of the therapy delivery parameters (e.g., the amplitude, pulse width, frequency, bi-polar pairs, and order of pairs for therapy) as outlined in the look-up table of rules in memory 82. The process then returns to step 708, where output from the sensor 86 is received.

If at step 712 therapy is not being currently delivered, the inquiry is whether the detected posture from step 710 requires delivery of therapy at step 718. If no, then the process returns to step 708, where output from the sensor 86 is received. If the detected posture from step 710 does require therapy at step 718, the process moves to step 720 where the appropriate therapy for the detected position is determined. The appropriate therapy may be read from the look-up table stored in memory 82 by control circuit 80 so that it can direct the therapy delivery circuit 84 accordingly. Once therapy is initiated at step 722, the process returns to step 708 and the output of the sensor 86 is monitored for changes in posture.

In the method above, the starting and stopping of therapy can become automated requiring little to no input from the patient. However, the patient will always have the ability to override therapy delivery through use of the external programmer 50.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single module or unit for purposes of clarity, it should be understood that the techniques of this disclosure may be performed by a combination of units or modules associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, an implantable medical device system has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

We claim:

1. An implantable neurostimulator (INS) comprising:
an electrical lead having formed thereon at least a pair of bi-polar electrodes, wherein the electrical lead is configured for placement of the pair of bi-polar electrodes proximate protrusor muscles of a patient;
a pulse generator electrically connected to the electrical lead and configured to deliver electrical energy to the pair of bi-polar electrodes, the pulse generator having mounted therein a sensor and a control circuit,
wherein the sensor is configured to generate signals representative of an orientation of the pulse generator and communicate the signals to the control circuit and the control circuit is configured to determine the orientation of the pulse generator and deliver electrical energy to the bi-polar electrodes when the determined orientation correlates to a pre-determined orientation, and wherein the sensor and control circuit are configured to detect electromyography signals of the protrusor muscles and the control circuit is configured to determine a fatigue of the protrusor muscles based on the detected electromyography signals.

2. The implantable neurostimulator of claim 1, wherein the sensor is a three-axis accelerometer.

3. The implantable neurostimulator of claim 1, wherein the determined orientation is indicative of a patient in which the INS is implanted is supine.

4. The implantable neurostimulator of claim 1, further comprising a memory storing therein a correlation of the signals from the sensor to orientations of the pulse generator.

5. The implantable neurostimulator of claim 4, wherein the memory stores therein a plurality of stimulation control parameters.

6. The implantable neurostimulator of claim 5, wherein each stimulation control parameter is associated with an orientation of the pulse generator.

7. The implantable neurostimulator of claim 6, wherein the sensor is further configured to detect one or more of motion, heartrate, or sound.

8. The implantable neurostimulator of claim 7, wherein the control circuit delivers electrical energy to the bi-polar electrodes when the determined orientation correlates to a pre-determined orientation and one or more of a detected motion, heartrate, or sound correspond to a determination that the patient is asleep or in need of therapy.

9. The implantable neurostimulator of claim 1, wherein the at least one pair of bi-polar electrodes comprises at least a first and second pair of bi-polar electrodes.

10. The implantable neurostimulator of claim 9, wherein the pulse generator further comprises a therapy delivery circuit configured to deliver the electrical energy to the bi-polar electrodes, the therapy delivery circuit including a charging circuit, an output circuit, and a switching circuit, the switching circuit selectively coupled to the bi-polar electrodes to deliver the electrical energy to different portions of the protrusor muscles at different times to avoid fatigue, without requiring delivery to be withheld completely.

11. A method comprising:
   storing in memory of an implanted neurostimulator (INS) a correlation of postures of a patient to an orientation of the INS;
   receiving sensor data indicative of the INS being in an orientation that correlates to a posture in which the patient is likely to experience obstructive sleep apnea;
   determining whether the patient is in a sleep state or in need of therapy using a control circuit;
   delivering electrical energy from a therapy delivery circuit of the INS to a pair of bi-polar electrodes to activate the patient's protrusor muscles;
   detecting electromyography signals of the protrusor muscles using the sensor; and
   determining fatigue of the protrusor muscles based on the detected electromyography signals using the control circuit.

12. The method of claim 11, wherein the sensor is a three-axis accelerometer.

13. The method of claim 11, wherein the detected orientation of the INS is indicative of a posture in which the patient is supine.

14. The method of claim 11, further comprising storing in memory in the INS a correlation of the received sensor data to postures of the patient.

15. The method of claim 14 further comprising storing in memory a plurality of stimulation control parameters.

16. The method of claim 15, wherein each stimulation control parameter is associated with an orientation of the INS.

17. The method of claim 15, further comprising detecting one or more of motion, heartrate, or sound.

18. The method of claim 17, further comprising determining the patient is in a sleep state or in need of therapy based on the sensor data indicative of the INS orientation and one or more of the detected motion, heartrate, or sound.

* * * * *